(12) United States Patent
Kuo et al.

(10) Patent No.: US 7,277,746 B2
(45) Date of Patent: Oct. 2, 2007

(54) METHOD AND APPARATUS FOR ANALYZING HEART RATE VARIABILITY

(76) Inventors: Terry B. J. Kuo, 7F-2, No. 52, Beichang 5th St., Ji-An Township, Hualien County 973 (TW); Cheryl C. H. Yang, 7F-2, No. 52, Beichang 5th St., Ji-An Township, Hualien County 973 (TW)

( * ) Notice: Subject to any disclaimer, the term of this patent is extended or adjusted under 35 U.S.C. 154(b) by 0 days.

(21) Appl. No.: 10/790,508

(22) Filed: Mar. 1, 2004

(65) Prior Publication Data

US 2004/0230130 A1 Nov. 18, 2004

(30) Foreign Application Priority Data

May 14, 2003 (TW) ................................ 92113073 A

(51) Int. Cl.
*A61B 5/04* (2006.01)

(52) U.S. Cl. .................................................... 600/509

(58) Field of Classification Search ................ 600/515, 600/508, 509, 516, 517, 519, 521
See application file for complete search history.

(56) References Cited

U.S. PATENT DOCUMENTS 6,512,945 B1 * 1/2003 Hoium et al. ................ 600/515

OTHER PUBLICATIONS

Camm, A. John; Malik, Marek; "Heart rate variability: Standards of measurement, physiological intrepretation, and clinical use"; _European Heart Journal_; Mar. 1996; pp. 354-381; vol. 17; Task Force of The European Society of Cardiology and the North American Society of Pacing and Electrophysiology; UK.

* cited by examiner

*Primary Examiner*—George Manuel
(74) *Attorney, Agent, or Firm*—Egbert Law Offices

(57) ABSTRACT

A user-friendly and statistic based heart rate variability analytical method includes the following steps of capturing an electrocardiogram signal of a person, performing analog-to-digital conversion of the electrocardiogram signal, selecting the peaks of the electrocardiogram signal, calculating the standard deviation of the heights, durations and inter-peak intervals of the peaks, removing the peaks whose heights, durations or inter-peak duration fall beyond a first predetermined standard deviation, sampling and interpolating the qualified peaks to form a consecutive peak signal, and performing spectrum analysis to the peak signal in frequency domain.

9 Claims, 5 Drawing Sheets

METHOD AND APPARATUS FOR ANALYZING HEART RATE VARIABILITY

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention is related to an analytical method and an apparatus of heart rate variability, more specifically, to programmable analytical method and apparatus of heart rate variability, designed to be used by various users with ease.

BACKGROUND OF THE INVENTION

Sympathetic nerves and parasympathetic nerves, both of which belong to human autonomic nervous system, are closely related to the daily operation of a human body. Autonomic imbalance may induce various acute and chronic diseases, for example, heart disease, hypertension, etc., and may even lead to a sudden death, if serious. Even healthy individuals suffering from autonomic disorders may have palpitation, dyspnea (shortness of breath), gastrointestinal disorders, insomnia, etc. Hence, the protection for autonomic nervous system is not only an important issue in medicine but also a personal concern to an individual everyday. Living quality depends on how well our autonomic nervous system functions. Signs and symptoms of certain severe diseases at an early stage are attributable to autonomic disorders. Hence, early detection of autonomic disorder in an individual or a patient is likely to lessen or even prevent tragedies.

In the past, numerous instruments and methods for evaluation of autonomic functions were developed, including heart rate variation with deep breathing, valsalva response, sudomotor function, orthostatic blood pressure recordings, cold pressure test, biochemistry test, etc. However, the abovementioned methods either cause the patients much pain by requiring them to immerse in water during the test, or require expensive instruments. Hence, the above-mentioned methods are not fit to be used widely. In addition, some of these methods are difficult to use because of poor precision.

A normal adult's heart rate is about 70 beats per minute. The regular beating originates in a pacemaking system of the heart, which comprises sinoatrial node (SA node), atrioventricular node (AV node) and various kinds of nerve fibers. The pacemaking system is very precise so as to maintain the most essential rhythm of life. Nevertheless, to cope with various environments inside and outside human bodies, human bodies are equipped with the autonomic nervous system including the sympathetic nervous system and the parasympathetic nervous system for regulation of heart rate. The former increases the heart rate, whereas the latter decreases it. Owing to the interaction of the two nervous systems, heart rate is kept in an optimal state of equilibrium.

In addition to their different effects, the two nervous systems function at different speeds. The sympathetic nerves work slowly, and the parasympathetic nerves (especially the vagus nerve, which controls heart rate) function fast. Mankind has known the discrepancy between the respective speeds of these two different kinds of nervous systems for a long time. However, in the past, the analytical instruments were not sophisticated enough to enable the evaluation of this characteristic or persuade people that it is worth using.

Moreover, as discovered by researchers, although a normal adult's heart maintains at around 70 beats per minute during a static state, there are some regular or irregular fluctuations in the hear rate. Fast or slow, regular or random, the fluctuations were usually ignored in medical researches conducted in the past because of their minute amplitudes. Nonetheless, according to some experts, part of the fluctuations keeps pace with breathing, though the remainder has nothing to do with breath. In this regard, little can be achieved with conventional analytical methods for two reasons. First, the amplitudes of the fluctuations are too small to be observed by means of any conventional recorder, and thus researchers have to adopt invasive experimental methods in order to excite the fluctuations to such an extent that it is feasible to measure them. Secondly, there was not any method suitable for the quantitative, statistical analysis of the fluctuations despite their occurrence.

In recent years, plenty of new technologies to evaluate the autonomic functions were successfully developed. Given the sophisticated computer hardware and software know-how available, today it is possible to detect and perform quantitative analysis of a person autonomic cardiac activity in light of the minute fluctuations of hear rate, known as heart rate variability (HRV), taken while the person is at rest. In other words, the new technologies allow a user to analyze or evaluate a normal person's autonomic functions without interfering with the person's daily life. Heart rate variability analysis stands out above other methods for evaluation of autonomic functions, because it has the following advantages: (1) being a non-invasive diagnosis technology, it does not cause a subject any pain, (2) the hardware it uses is cheap, thus it has the potential for large-scale promotion, and (3) many animal tests and human tests prove that it evaluates autonomic functions accurately. Therefore, the technology of heart rate variability analysis is in wide use in recent years, and related research is conducted on it unceasingly.

The advent of the technology about spectrum analyzers in the early 1980s enabled heart rate variability analysis to be brought into full play, when autonomic functions were quantitatively analyzed in light of the beating cycle of heart. Hence, heart rate variability analysis gradually becomes the best non-invasive method for detecting autonomic functions.

With spectrum analysis, researchers discovered that the minute fluctuations of heart rate variability can be definitely divided into two groups, that is, high-frequency (HF) component and low frequency (LF) component. The HF component is synchronous to animals breath signals, so it is also known as breath component, which occurs approximately every three seconds in a human being. The source of the LF component that takes place approximately every ten seconds in a human being remains unidentified, though researchers infer that they are relevant to vascular motion or baroreflex. Some academics went further to divide the LF component into two categories, that is, very low frequency (VHF) component and low frequency component. At present, many physiologists and cardiologists believe that the HF component or total power (TP) reflects parasympathetic functions, whereas the ratio of LF component to HF component (LF/HF) reflects sympathetic activity. In addition to being an index of autonomic functions, heart rate variability reflects various kinds of information about human bodies, as indicated by some researches. For instance, patients diagnosed with intracranial hypertension usually have relatively low heart rate variability, the death rate of an elder whose LF component of heart rate variability decreases by a standard deviation is 1.7 times that of normal persons, and the LF component of heart rate variability vanishes in a brain-dead person. Furthermore, there are changes in heart rate variability in a patient who exhibits rejection reactions after heart transplantation. During an operation, heart rate variability reflects depth of anesthesia. Gender and age certainly determine sympathetic functions and parasympathetic functions. For example, sympathetic functions and parasympathetic functions are active in young persons, but rather inactive in old persons; in males, sympathetic functions prevail but parasympathetic functions yield; conversely, parasympathetic functions excel sympathetic functions in females. Afterward, the fact that women's sympathetic functions increase during pregnancy, is found in hospitals, but any overreaction may be complicated by, or even contribute to, life-threatening preeclampsia.

In 1996, European and American cardiology societies standardized and published the analytical method of heart rate variability (Circulation (1996), 17, pp. 354-381), which is shown in the flowchart of FIG. 1. In the first place, capturing an electrocardiogram signal, and then digital sampling and noise filtering are performed by a microprocessor. Sequentially, the RR data (RR peak-to-peak intervals) of the captured electrocardiogram signal is edited, and any unsatisfactory RR peak-to-peak intervals is removed to acquire the RR peak-to-peak intervals generated by normal rhythmic points, which is called NN data. The heart rate variability is acquired by conducting spectrum analysis of frequency domain followed by performing interpolation and sampling to the NN data. However, this method is rather complicated and trivial, and researchers have to identify noise, edit RR data and eliminate them manually, and thus it requires considerable manpower and time to accomplish the chores. Hence, the aforesaid method constitutes a high threshold for laymen to gain access to the method.

At present, heart rate variability is mostly analyzed by a digital computer. An electrocardiogram signal is captured and analog-to-digital conversion is performed on it, and then the converted electrocardiogram signal is stored in a digital file. Meanwhile, it is necessary to provide an identification code or a filename for the digital file. Any correction or analysis carried out to the digital file has to be done manually. Upon completion of the analysis, data also has to be printed out manually.

In short, with a conventional method, the process of analysis of heart rate variability, from signal retrieval to file analysis and eventually printout processing, has to be performed manually. In this regard, a keyboard is the usual medium of operation. As a result, the analytical process of heart rate variability involves a lot of keystrokes performed on the part of a researcher and, worse yet, it also involves pressing different types of keys on the keyboard. In addition, equipped with a keyboard, a machine designed to analyze heart rate variability design can never be smaller; this does not conform to the current trend of miniaturization of machines.

BRIEF SUMMARY OF THE INVENTION

The primary objective of the present invention is to provide an analytical method and an apparatus of heart rate variability, with a view to simplifying the analytical process and carrying out automation. Furthermore, the present invention involves filtering out noise by means of statistical method, in order to enhance the precision of the analysis of heart rate variability.

The heart rate variability analytical method of the present invention comprises the steps of (1) capturing an electrocardiogram signal of a person; (2) performing analog-to-digital conversion of the electrocardiogram signal; (3) selecting the peaks of the electrocardiogram signal; (4) removing unqualified peaks; (5) sampling and interpolating the qualified peaks to form a consecutive peak signal; and (6) performing spectrum analysis to the peak signal in frequency domain. Moreover, the peak-to-peak interval also can be filtered to remove noise.

The step of removing unqualified peaks and peak-to-peak intervals is implemented as follows. The standard deviations of the heights, durations of the peaks or the peak-to-peak intervals are calculated first, and if an electrocardiogram signal whose height, duration or peak-to-peak interval exceeds a corresponding predetermined standard deviation, it will be deemed a noise and be removed.

The heart rate variability analytical apparatus of the present invention comprises an electrocardiogram signal detector, a signal amplifier, an analog-to-digital converter, a computer and a digital input/output device, where the electrocardiogram signal detector is used for capturing the electrocardiogram signal of a person, the signal amplifier is used for amplifying the electrocardiogram signal, the analog-to-digital converter is connected to the signal amplifier for digitizing the electrocardiogram signal, the computer connected to the analog-to-digital converter comprises a program for calculating, filtering and analyzing the digitized electrocardiogram signal and controlling the steps of the heart rate variability analysis, and the digital input/output device is connected to the computer as a user-machine communication interface of the heart rate variability analytical apparatus. Moreover, the digital input/output device can be connected to an "EXECUTE" button to execute the above mentioned heart rate variability analytical method.

In accordance with the present invention, the "EXECUTE" button of the present invention can replace a traditional keyboard, and the process can be automatically controlled by the program. As a result, the number of keystrokes can be reduced to one to accomplish all the above steps. Therefore, the method and apparatus put forth in the present invention may not only be applied to small machines, but also tremendously minimize operational errors.

DETAILED DESCRIPTION OF THE INVENTION

Figure 1:
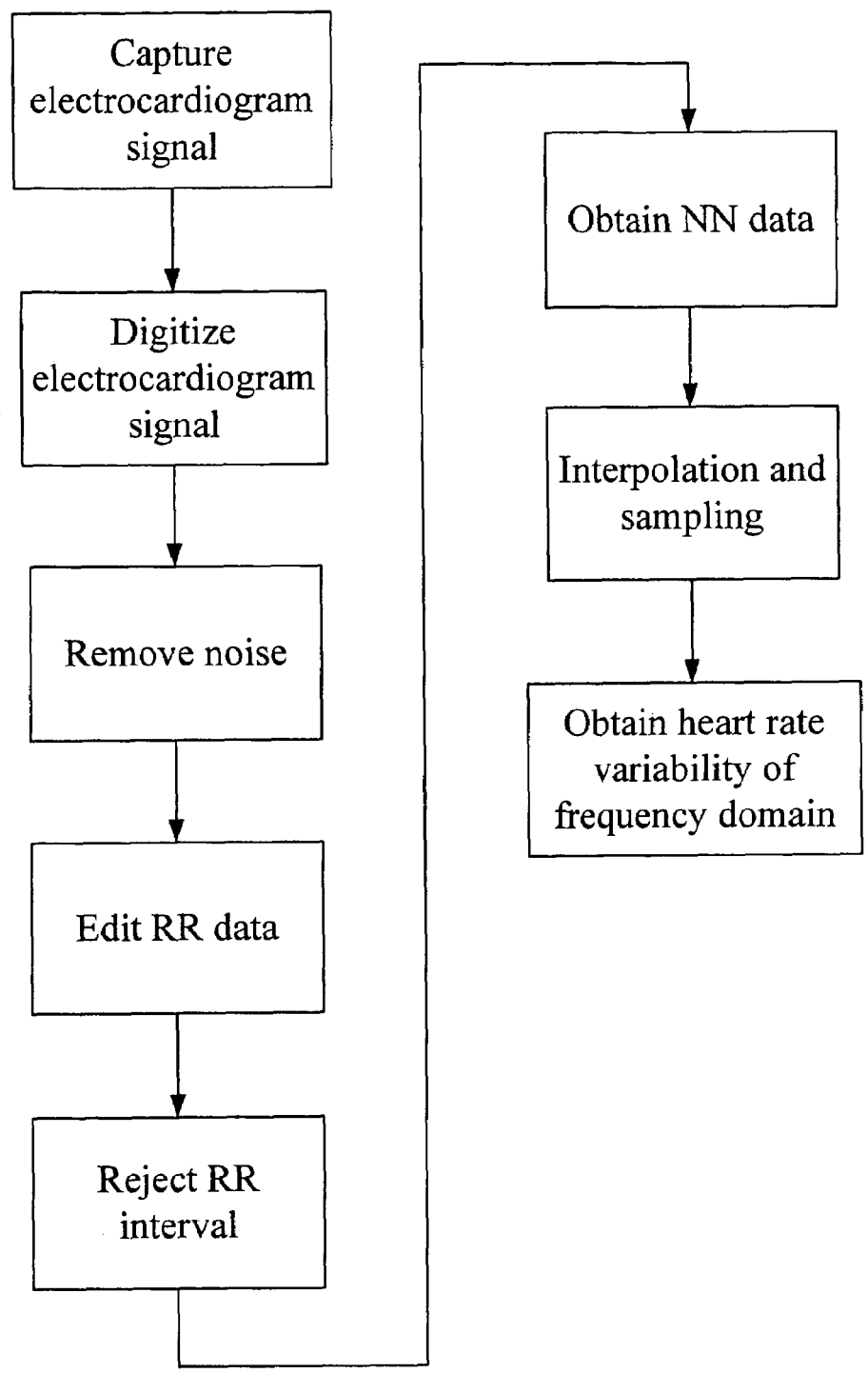
FIG. 1 is a schematic diagram illustrating a known process flow of heart rate variability analysis.
Figure 2:
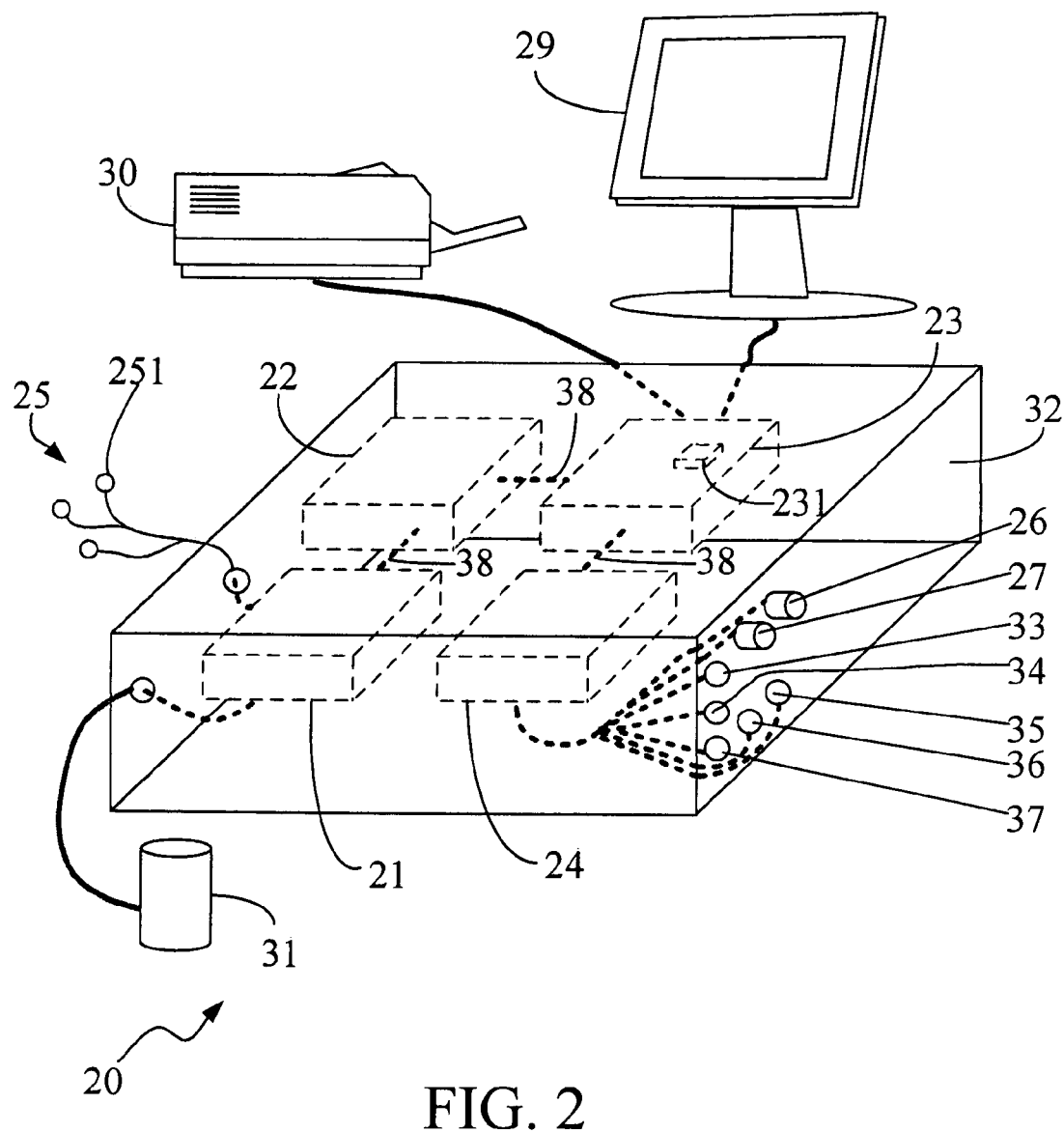
FIG. 2 is a perspective view illustrating the heart rate variability analytical apparatus of the present invention.

FIG. 2 depicts the heart rate variability analytical apparatus 20 as put forth in the present invention. It essentially comprises a signal amplifier 21, an analog-to-digital converter 22, a computer 23, a digital input/output device 24, an electrocardiogram signal detector 25, an "EXECUTION" button 26, and a case 32. The case 32 is a rectangular container whose dimensions are 14 cm×11 cm×4.5 cm, and it contains the signal amplifier 21, the analog-to-digital converter 22, the computer 23 and the digital input/output device 24. The electrocardiogram signal detector 25 is composed of three detection electrodes 251. One end of each detection electrode 251 is connected to the subject, and the other end passes through the case 32 to be connected to the signal amplifier 21 so as to capture a person electrocardiogram signals and transmit them to the signal amplifier 21. After being amplified by the signal amplifier 21, the electrocardiogram signals are converted into digital signals by means of the analog-to-digital converter 22, and then are entered into the computer 23. The computer 23 executes a program 231 to carry out a series of analyses and control-related tasks (for further details, please refer to later description). The digital input/output device 24 functions as the transmission interface between the computer 23 and the "EXECUTION" button 26. In practice, being a user-machine interface intended for external communication, the digital input/output device 24 may be additionally connected to a "NOISE" indicator 33, a "NO SIGNAL" indicator 34, a "PRINT" indicator 35, a "RECORDING" indicator 36, and a "STAND BY" indicator 37, to indicate the status of the heart rate variability analytical apparatus 20. Moreover, the digital input/output device 24 may be connected to a "CANCEL" button 27 for the sake of manual interruption of the process. The above-mentioned buttons 26 and 27 as well as various indicators 33-37 may be installed on the same side of the case 32 to facilitate control and surveillance. Cables 38 connect the signal amplifier 21 and the analog-to-digital converter 22, the analog-to-digital converter 22 and the computer 23, and the computer 23 and the digital input/output device 24 to transmit signals.

In addition, the computer 23 may be connected to a display 29 and a printer 30, so as to display and print the findings of the heart rate variability analysis of the electrocardiogram signals. The signal amplifier 21 may be connected to a battery 31 or an AC power source to meet its electric demand.

Figure 3:
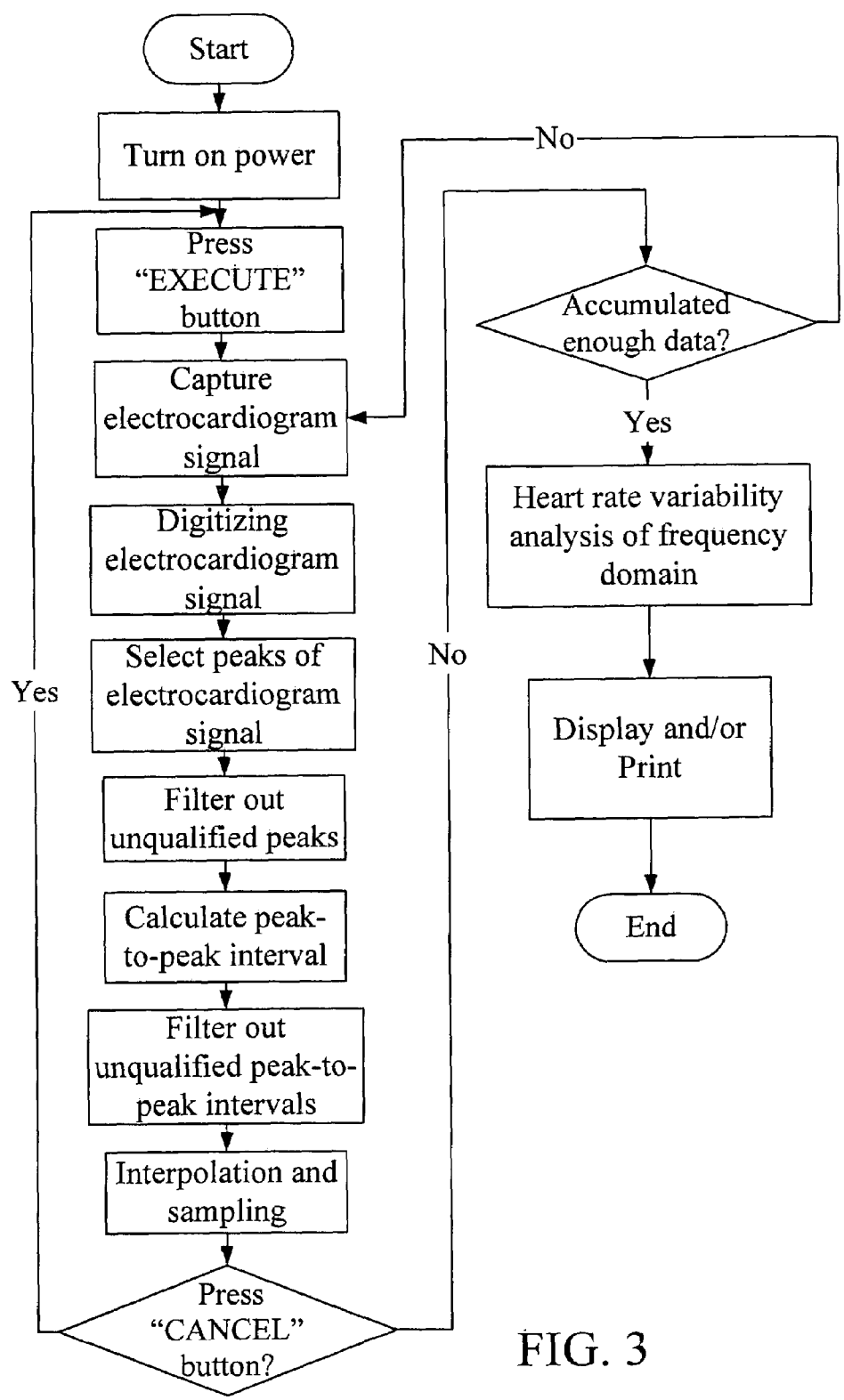
FIG. 3 is a schematic view illustrating the heart rate variability analytical process of the present invention.

The process of heart rate variability analysis put forth in the present invention is shown in FIG. 3. The following is the explanation of the analytical process, with references made to the heart rate variability analytical apparatus 20 depicted in FIG. 2.

Figure 4:
FIG. 4 is a graph illustration showing the QRS wave adopted by the heart rate variability analytical method of the present invention.

The "STAND BY" indicator 37 gets turned on as soon as the power for the heart rate variability analytical apparatus 20 is switched on, telling the user that the heart rate variability analytical apparatus 20 is standing by. All the procedures of the heart rate variability analysis are started by the "EXECUTION" button 26. Immediately after the user pressed the "EXECUTION" button 26, the "RECORDING" indicator 36 turns on, and the electrocardiogram signal detector 25 begins to capture a transient electrocardiogram signal which is then amplified by the signal amplifier 21 or additionally undergoes wave filtration performed with a band pass filter before being sent to the analog-to-digital converter 22. After that, the user performs analog-to-digital conversion, and carries out sampling at a rate of 256 to 2048 times per second on the electrocardiogram signal by means of the analog-to-digital converter 22, which is under the control of the program 231. In the meantime, the program 231 may have an additional function of detecting the 50/60 Hz components of the electrocardiogram signal. The "NOISE" indicator 33 gets turned on whenever the signal is too strong. The peak of the electrocardiogram signal corresponding to each heartbeat, i.e., the QRS wave, is searched out (please refer to FIG. 4), and it stands for each heartbeat. The "NO SIGNAL" indicator 34 turns on whenever no peak is identified. The program 231 measures parameters such as height and duration of the peak of each heartbeat, and calculates the mean and standard deviation of individual parameters in order to create a standard template. Afterward, each of the heartbeat peaks is compared with the template. In comparison, a heartbeat peak found to fall beyond a first predetermined standard deviation of the standard template is deemed a noise and, therefore, should be deleted. In practice, the first predetermined standard deviation is mostly set to three standard deviations.

The interval between the respective peaks of two successive heart-beats is measured to be the period of heartbeat at that point. The mean and standard deviation of all the heartbeat intervals are figured out, and then all the heartbeat intervals are verified. A heartbeat interval which falls beyond a second predetermined standard deviation is deemed as either a noise or an unstable signal, and thus it has to be deleted. Similarly, the second predetermined standard deviation is generally set to be as large as three standard deviations. All qualified peaks are sampled at an appropriate frequency, e.g., 7.11 Hz, and performed interpolation to keep the time consecution, with the program 231 to detect and see whether the "CANCEL" button 27 is pressed. If it is, the heart rate variability analytical apparatus 20 returns to the standby status; otherwise, the next step proceeds. Moreover, the program 231 is used to judge whether the amount of data is enough. If negative, the heart rate variability analytical apparatus 20 continues to capture electrocardiogram signals so as to form a loop; otherwise, the next step proceeds.

Figure 5:
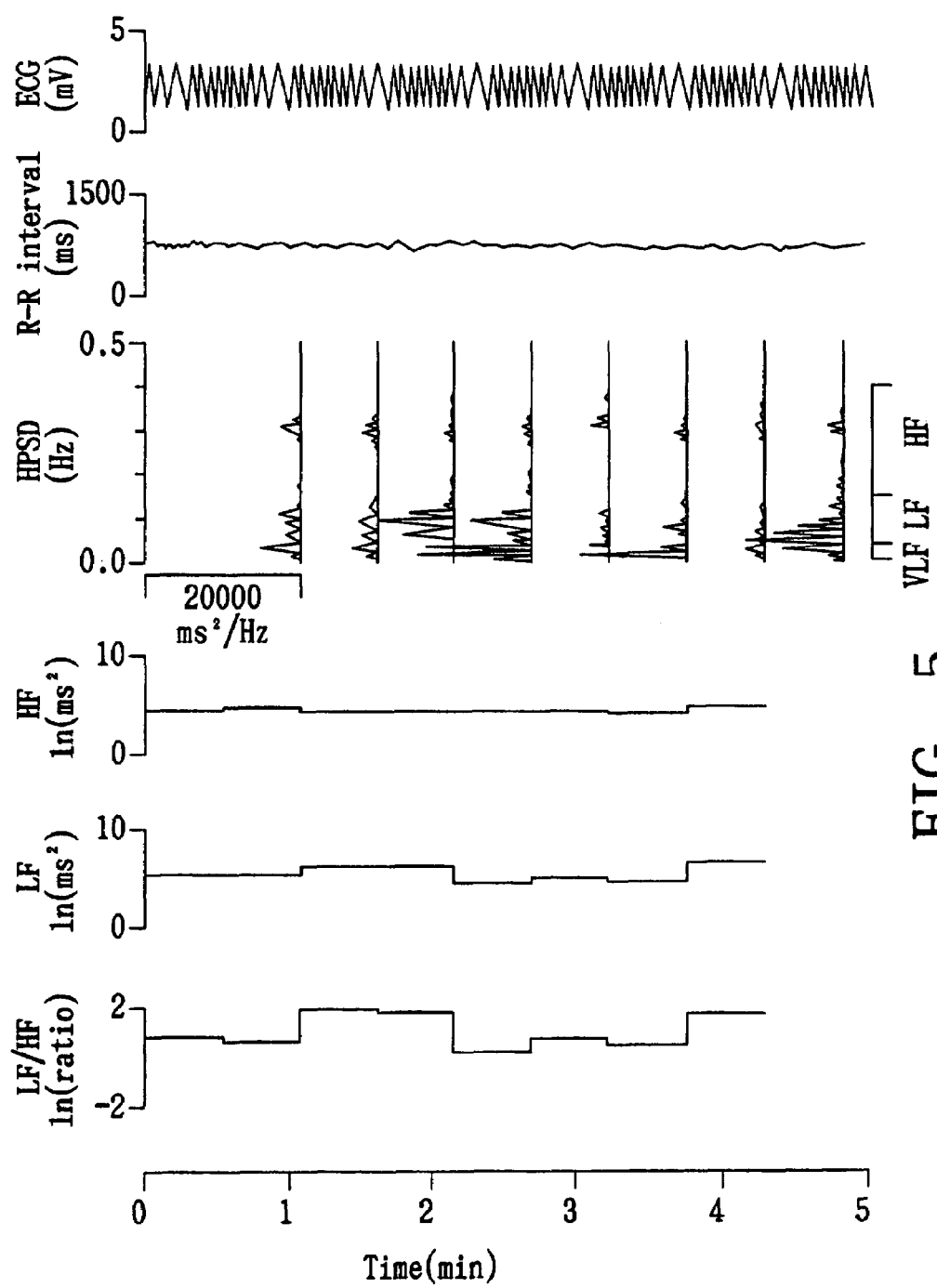
FIG. 5 is another graph illustration showing the heart rate variability analysis result of the present invention.

Fourier transform is adopted in spectrum analysis. In the first place, any linear drift of signal is eliminated to evade the interference from low-frequency band, and the Hamming computation is employed to prevent the mutual leakage between individual frequency components of the spectrum. After that, 288-second data (2048 points) is taken and fast Fourier transform is conducted so as to acquire heart rate power spectral density (HPSD), and the compensation with regard to any effects of sampling and Hamming computation is performed. The powers of the LF (0.04-0.15 Hz) and HF (0.15-0.4 Hz) bands of the heart rate power spectral density are quantified by integral, and the quantitative parameters like LF/HF or TP are figured out as well, as shown in FIG. 5.

Eventually, the findings are displayed on the display 29 or printed out with the printer 30. The "PRINT" indicator 35 turns on whenever the printer 30 is printing. In addition to external installation, the display 29 and the printer 30 may also be built-in, that is, installed inside the heart rate variability analytical apparatus 20.

The program 231 not only measures, filters and analyzes electrocardiogram signals, but, as illustrated with the present embodiment, also has the additional function of controlling the steps of the aforesaid heart rate variability analytical method, so a user merely needs to press the "EXECUTION" button 26 to accomplish all the steps.

Unlike a conventional heart rate variability analysis that requires a user to enter a large amount of data, the present invention reduces the number of keystrokes to one during the process of heart rate variability analysis, and even the traditional keyboard can be replaced with a button, under the integrated control of the computer program. The method put forth in the present invention may not only be applied to small machines, but also provide a friendly operating interface. Besides tremendously minimizing operational errors, it becomes accessible to laymen. In practice, the heart rate variability analytical apparatus put forth in the present invention is quite time-saving and easy to use, as it prints out a person heart rate variability analytical result and autonomic function data in just five minutes after a button is pressed.

The above-described embodiments of the present invention are intended to be illustrative only. Numerous alternative embodiments may be devised by those skilled in the art without departing from the scope of the following claims.

We claim:

1. A method of analyzing heart rate variability comprising the steps of:
   capturing an electrocardiogram signal of a person;
   performing an analog-to-digital conversion of said electrocardiogram signal;
   selecting peaks of said electrocardiogram signal;
   calculating a standard deviation of heights or durations of the peaks;
   removing the peaks having heights or durations that exceed a first predetermined standard deviation;
   calculating peak-to-peak intervals of said electrocardiogram signal;
   filtering out unqualified peak-to-peak intervals;
   sampling and interpolating qualified peaks and the peak-to-peak intervals so as to form consecutive peak signals; and
   performing a spectrum analysis upon the consecutive peak signals in a frequency domain.

2. The method of claim 1, said first standard deviation being substantially equivalent to three standard deviations.

3. The method of claim 1, the step of filtering out comprising the steps of:
   calculating a standard deviation of the peak-to-peak intervals of said electrocardiogram signal; and
   removing the peak-to-peak intervals that exceed a second predetermined standard deviation.

4. The method of claim 3, said second predetermined standard deviation being substantially equivalent to three standard deviations.

5. The method of claim 1, wherein each of the steps is accomplished by a button-inputted command.

6. The method of claim 1, further comprising the step of:
   checking to determine if the sampling data is sufficient.

7. The method of claim 1, further comprising:
   displaying a result of the spectrum analysis.

8. The method of claim 7, said step of displaying comprising:
   printing out the result.

9. The method of claim 1, the peaks being QRS waves.

* * * * *